United States Patent
Baur et al.

(10) Patent No.: US 11,103,496 B2
(45) Date of Patent: Aug. 31, 2021

(54) METHODS FOR ENHANCING LIVER REGENERATION

(71) Applicant: The Trustees of the University of Pennsylvania, Philadelphia, PA (US)

(72) Inventors: Joseph Baur, Merion Station, PA (US); Sarmistha Mukherjee, Blue Bell, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 38 days.

(21) Appl. No.: 16/078,446

(22) PCT Filed: Feb. 22, 2017

(86) PCT No.: PCT/US2017/018929
§ 371 (c)(1),
(2) Date: Aug. 21, 2018

(87) PCT Pub. No.: WO2017/147180
PCT Pub. Date: Aug. 31, 2017

(65) Prior Publication Data
US 2019/0099409 A1  Apr. 4, 2019

Related U.S. Application Data

(60) Provisional application No. 62/298,139, filed on Feb. 22, 2016.

(51) Int. Cl.
| | | |
|---|---|---|
| *A61K 31/455* | (2006.01) | |
| *A61K 45/06* | (2006.01) | |
| *A61K 31/706* | (2006.01) | |
| *A61P 1/16* | (2006.01) | |

(52) U.S. Cl.
CPC .......... *A61K 31/455* (2013.01); *A61K 31/706* (2013.01); *A61K 45/06* (2013.01); *A61P 1/16* (2018.01)

(58) Field of Classification Search
None
See application file for complete search history.

(56) References Cited

U.S. PATENT DOCUMENTS

| | | | | |
|---|---|---|---|---|
| 4,499,076 A | * | 2/1985 | Ohashi | A61K 38/01 424/637 |
| 7,829,556 B2 | | 11/2010 | Bemis et al. | |
| 8,247,565 B2 | | 8/2012 | Bemis et al. | |
| 2010/0061963 A1 | * | 3/2010 | Peled | C12N 5/0647 424/93.7 |
| 2011/0015192 A1 | | 1/2011 | Bemis et al. | |
| 2012/0208172 A1 | * | 8/2012 | Karp | A61P 43/00 435/1.1 |
| 2013/0338178 A1 | | 12/2013 | Shenk et al. | |
| 2014/0221319 A1 | | 8/2014 | Sinclair et al. | |
| 2015/0175645 A1 | | 6/2015 | Milburn et al. | |

FOREIGN PATENT DOCUMENTS

| | | |
|---|---|---|
| CN | 103565818 A | 2/2014 |
| JP | 6727317 | 7/2020 |
| WO | 2006001982 A2 | 1/2006 |
| WO | 2015069860 A1 | 5/2015 |

OTHER PUBLICATIONS

García-Rodríguez, J. L., . . . & Trauner, M. (2014). SIRT1 controls liver regeneration by regulating bile acid metabolism through farnesoid X receptor and mammalian target of rapamycin signaling. Hepatology, 59(5), 1972-1983. (Year: 2014).*
Wang, B., Ma, Y., Kong, X., Ding, X., Gu, H., Chu, T., & Ying, W. (2014). NAD+ administration decreases doxorubicin-induced liver damage of mice by enhancing antioxidation capacity and decreasing DNA damage. Chemico-biological interactions, 212, 65-71. (Year: 2014).*
Bai, P. Cantó, C., Oudart, H., Brunyánszki, A., Cen, Y., Thomas, C., . . . & Schoonjans, K. (2011). PARP-1 inhibition increases mitochondrial metabolism through SIRT1 activation. Cell metabolism, 13(4), 461-468. (Year: 2011).*
International Search Report for PCT/US2017/018929; dated May 8, 2017; 4 pages.
Written Opinion for PCT/US2017/018929; dated May 8, 2017; 8 pages.
Canto et al. "The NAD+ precursor nicotinamide riboside enhances oxidative metabolism and protects against high-fat diet induced obesity." Cell Metab; Jun. 6, 2012 (Jun. 6, 2012), vol. 15, Iss. 6, pp. 838-847; entire document.
Kulikova et al. "Generation, release and uptake of the NAD pre-cursor nicotinic acid riboside by human cells." J. Biol Chem., Sep. 18, 2015 (Sep. 18, 2015), vol. 290, Iss. 45, pp. 27124-27137; entire document.
English translation of Japanese Office Action for JP 2018-544173 ; dated Oct. 3, 2019; 7 pages.
Hepatology; Dec. 16, 2015, vol. 63, No. 4, pp. 1190-1204; 16 pages.
International immunopharmacology; 2012, vol. 14, pp. 530-537; 9 pages.
European Search Report for EP 17 757 141 dated Sep. 24, 2020; 5 pages.

(Continued)

*Primary Examiner* — Dale R Miller
(74) *Attorney, Agent, or Firm* — Morgan, Lewis & Bockius LLP

(57) ABSTRACT

The invention includes methods, kits, and pharmaceutical compositions for enhancing liver regeneration in a mammal in need thereof, comprising administering a therapeutically effective amount of an agent that increases nicotinamide adenine dinucleotide (NAD) activity. The methods may include administering a therapeutically effective amount of an agent that increases nicotinamide adenine dinucleotide (NAD) activity and a sirtuin 1 (Sirt1) agonist. The agent that increases NAD activity may be a NAD precursor. The NAD precursor may include one or more of tryptophan, nicotinic acid, nicotinic acid riboside, nicotinamide riboside (NR), nicotinamide, NADP, and NAD itself and a pharmaceutically acceptable salt thereof.

17 Claims, 6 Drawing Sheets

(56) References Cited

OTHER PUBLICATIONS

European Supplementary Search Report for EP 17 757 141 dated Sep. 17, 2020; 3 pages.
European Opinion for EP 17 757 141 dated Sep. 24, 2020; 5 pages.
European Communication for EP 17 757 141; dated Sep. 24, 2020; 1 page.
Bonkowski, et al.; Nature Reviews (2016) 17: 679-690.
Hu et al.; "Long-Term Expansion of Functional Mouse and Human Hepatocytes as 3D Organoids"; dated Nov. 28, 2018; Cell 175, 1591-1606.
Gariani; "Eliciting the Mitochondrial Unfolded Protein Response by Nicotinamide Adenine Dinucleoride Repletion Reverses Fatty Liver Disease in Mice"; Hepatology, Sep. 24, 2015; URL: https://aasidpubs.onlinelibrary.wiley.com/doi/epdf/10.1002/hep.2824; pp. 1190-1204.
Ganji et al.; "Therapeutic role of niacin in the prevention and regression of hepatic statosis in rat model of nonalcoholic fatty liver disease"; American Journal of Physiology—Gastrointestinal and Liver Physiology; vol. 306, No. 4; Feb. 15, 2014; pp. G320-G327.
Mukherjee et al.; "Nicotinamide adenine dinucleotide biosynthesis promotes liver rejeneration: Mukherjee et al."; Hepatology; vol. 65, No. 2; Dec. 24, 2016; pp. 616-630.

Notice of Allowance for Japanese Patent Application No. 2018-544173; dated Jun. 2, 2020; 59 pages.
Chinese Office Action for Chinese Patent Application No. 201780024854.5; dated Aug. 13, 2020; 4 pages.
English translation of Chinese Office Action for Chinese Patent Application No. 201780024854.5; dated Aug. 13, 2020; 4 pages.
Chinese Search Report for Chinese Patent Application No. 201780024854.5; dated Aug. 10, 2020; 3 pages.
English translation of Chinese Search Report for Chinese Patent Application No. 201780024854.5; dated Aug. 10, 2020; 3 pages.
Jin X et al., "Exogenous interleukin-6 enhances liver regeneration after major and extreme liver resection"; Journal of Surgical Research, 2015, vol. 130, No. 2, p. 320.
Sato F et al., "Effects of nicotinamide-related agents on the growth of primary rat hepatocytes and formation of small hepatocyte colonies"; Liver, 1999, vol. 19, No. 6, p. 481-488.
Chinese Second Office Action for CN201780024854.5; dated Jan. 15, 2021; 4 pages.
English translation of Chinese Second Office Action for CN201780024854.5; dated Jan. 15, 2021; 6 pages.
Communication from the EPO for EP Application No. 17 757 141.1; dated Mar. 11, 2021; 2 pages.
Annex to the Communication from the EPO for EP Application No. 17 757 141.1; dated Mar. 11, 2021; 5 pages.

\* cited by examiner

METHODS FOR ENHANCING LIVER REGENERATION

CROSS-REFERENCE TO RELATED APPLICATIONS

This application is the U.S. National Stage of International Patent Application No. PCT/US2017/018929, filed Feb. 22, 2017, which claims the benefit of priority to U.S. Provisional Application No. 62/298,139, filed Feb. 22, 2016, the entirety of which are incorporated herein by reference.

GOVERNMENT LICENSE RIGHTS

This invention was made with government support under R01 AG043483 and R01 DK098656 awarded by the National Institutes of Health. The government has certain rights in the invention.

FIELD OF THE INVENTION

The invention relates generally to methods and compositions for accelerating and/or enhancing liver regeneration and more particularly, but not exclusively, to the use of nicotinamide adenine dinucleotide (NAD) precursors and inhibitors of NAD consumption in methods, kits, and formulations for accelerating and/or enhancing liver regeneration before or after liver injury.

BACKGROUND OF THE INVENTION

The regenerative capacity of the liver is essential for recovery from surgical resection or injuries induced by trauma or chemicals. During liver regeneration, the concentration of nicotinamide adenine dinucleotide (NAD) falls, at least in part due to metabolic competition for precursors.

SUMMARY OF THE INVENTION

The invention meets the needs in the field by providing NAD precursors and inhibitors of NAD consumption as treatments for enhancing and accelerating liver regeneration.

In one aspect, the invention includes methods for enhancing liver regeneration in a mammal in need thereof. The methods may include administering a therapeutically effective amount of an agent that increases nicotinamide adenine dinucleotide (NAD) activity.

In some embodiments, the invention includes methods for enhancing liver regeneration in a mammal in need thereof. The methods may include administering a therapeutically effective amount of an agent that increases nicotinamide adenine dinucleotide (NAD) activity and a sirtuin 1 (Sirt1) agonist.

In some embodiments, the agent that increases NAD activity may be a NAD precursor. For example, the NAD precursor may include one or more of an intermediate of a de novo pathway for synthesizing NAD, an intermediate of a NAD salvage pathway, and an intermediate of a nicotinamide riboside kinase pathway.

In some embodiments, the intermediate of a de novo pathway for synthesizing NAD may include tryptophan, nicotinic acid, nicotinic acid adenine dinucleotide, nicotinic acid mononucleotide, quinolinic acid, 3-hydroxyanthranilate, 3-hydroxykynurenine, kynurenine, N-formylkynurenine, or a pharmaceutically acceptable salt thereof. In some embodiments, the intermediate of a NAD salvage pathway may include nicotinamide, nicotinamide mononucleotide, or a pharmaceutically acceptable salt thereof. In some embodiments, the intermediate of a nicotinamide riboside kinase pathway may include nicotinamide riboside, nicotinic acid riboside, or a pharmaceutically acceptable salt thereof.

In some embodiments, the NAD precursor may include one or more of tryptophan, nicotinic acid, nicotinic acid riboside, nicotinamide riboside (NR), nicotinamide, NADP, and NAD itself, and a pharmaceutically acceptable salt thereof.

In some embodiments, the agent that increases NAD activity may be an inhibitor of NAD consumption. The inhibitor of NAD consumption may be one or more of a poly adp-ribose polymerase (PARP) inhibitor, a CD38 inhibitor, and a pharmaceutically acceptable salt thereof.

In another aspect, the invention may include a kit for providing a method for enhancing liver regeneration in a mammal in need thereof. In some embodiments, the kit may include a therapeutically effective amount of a nicotinamide adenine dinucleotide (NAD) precursor or an inhibitor of NAD consumption in unit dosage form. In some embodiments, the kit may include a therapeutically effective amount of an agent that increases nicotinamide adenine dinucleotide (NAD) activity and a sirtuin 1 (Sirt1) agonist in unit dosage form.

In another aspect, the invention may include a pharmaceutical composition for enhancing liver regeneration in a mammal in need thereof. In some embodiments, the composition may include a nicotinamide adenine dinucleotide (NAD) precursor or an inhibitor of NAD consumption, and a physiologically compatible carrier medium. In some embodiments, the composition may include a therapeutically effective amount of an agent that increases nicotinamide adenine dinucleotide (NAD) activity and a sirtuin 1 (Sirt1) agonist, and a physiologically compatible carrier medium.

BRIEF DESCRIPTION OF THE DRAWINGS

The foregoing summary and the following detailed description of the exemplary embodiments of the invention may be further understood when read in conjunction with the appended drawings, in which.

DETAILED DESCRIPTION OF THE INVENTION

Figure 1:
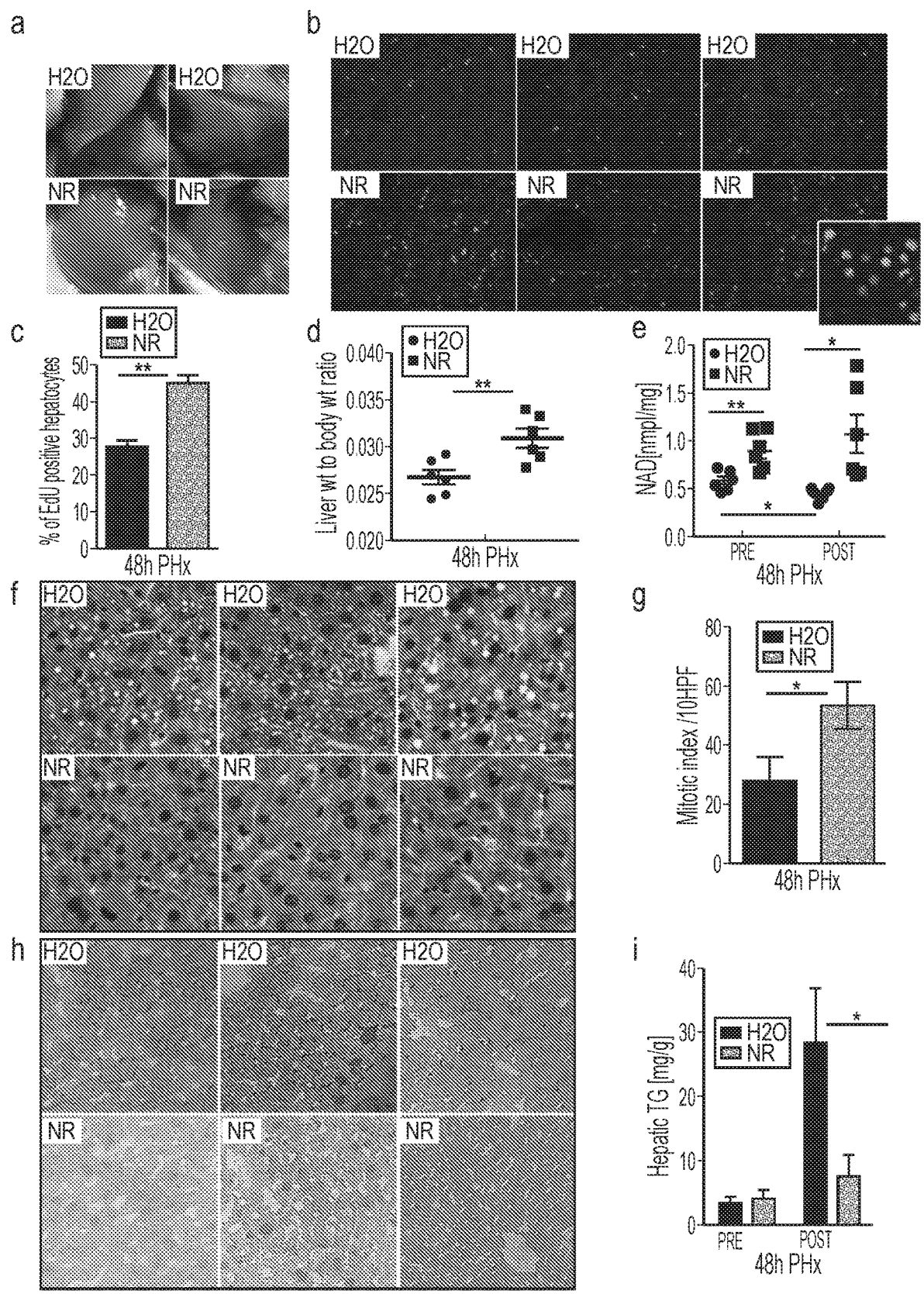
FIG. 1 illustrates that nicotinamide riboside promotes liver regeneration. 10-14 week old male C57BL6/J mice were treated with nicotinamide riboside (NR) at a dose of ~500 mg/kg/day. After 14 days, animals were subjected to ⅔ partial hepatectomy and analyzed 48 hours later (n=6 per group). (panel A) Photomicrographs of regenerated liver. (panel B) EdU incorporation in regenerating livers. Inset shows an enlarged view from an NR-treated liver. (panel C) Quantification of EdU positive hepatocytes. (panel D) Liver to body weight ratio. (panel E) Liver NAD content pre and post PHx. (panel F) Representative liver sections stained with H&E at 40× showing mitotic figures and micro and macro-vesicular fatty changes. (panel G)Quantification of mitotic figures across multiple high power fields. (panel H) Oil Red O staining to detect neutral lipids. (panel I) Hepatic triglyceride content in pre and post hepatectomized NR and placebo/H2O treated mice. Error bars represent S.E.M. *, p 0.05; , p 0.01; *, p 0.001.

The liver is one of the few structures that is capable of substantial regeneration in mammals, and can fully re-grow from less than 30% of its original mass. This regenerative capacity is critical to survival under conditions such as traumatic injury, exposure to hepatotoxins or infectious agents, or surgical resection. Recovery of liver function is highly dependent upon increasing energy production necessary for restoring liver mass. However, the mechanisms that are important for the liver to respond to acute and chronic injury and the biological pathways that govern the ability of the liver to regenerate are not well understood. As such, there is substantial interest in therapeutic approaches that could accelerate the regenerative process and speed the return to normal liver function in patients with liver injury.

In light of the foregoing, the invention provides methods, kits, and pharmaceutical compositions for enhancing liver regeneration, and treating liver disease, disorder, or injury in a mammal in need thereof. In some embodiments, the methods, kits, and pharmaceutical compositions may include agents that are nicotinamide adenine dinucleotide (NAD) precursor(s) and/or inhibitors of NAD consumption.

As used herein, a "nicotinamide adenine dinucleotide (NAD) precursor" is any small molecule that leads to an increase of NAD. The small molecule may be in a reduced or non-reduced form.

As used herein, an "inhibitor of NAD consumption" is an inhibitor that causes an increase in NAD availability. NAD availability includes an increase in total NAD in a cell or tissue, or an increase in the amount of NAD that is available to an enzyme of interest.

Methods of the Invention

In one aspect, a method of regenerating liver is encompassed. In some embodiments, a method of treating liver disease, disorder, or injury is provided. In each instance the method comprises increasing nicotinamide adenine dinucleotide (NAD).

Increasing NAD. In accordance with the invention, NAD activity and/or content may be increased by administering one or more agents that (1) are nicotinamide adenine dinucleotide (NAD) precursor(s); and/or (2) act as inhibitors of NAD consumption.

In some embodiments, NAD activity may be increased by administration of NAD or NADH as well as by synthesizing NAD. NAD may be synthesized through three major pathways, the de novo pathway in which NAD is synthesized from tryptophan, the NAD salvage pathway in which NAD is generated by recycling degraded NAD products such as nicotinamide, and the nicotinamide riboside kinase pathway in which nicotinamide riboside is converted to nicotinamide mononucleotide by nicotinamide riboside kinase. Thus, the NAD precursors of the invention may include one or more of an intermediate of a de novo pathway for synthesizing NAD, an intermediate of a NAD salvage pathway, and an intermediate of a nicotinamide riboside kinase pathway.

In some embodiments, where the NAD precursor includes an intermediate of a de novo pathway for synthesizing NAD, such intermediates may include, without limitation, tryptophan, nicotinic acid, nicotinic acid adenine dinucleotide, nicotinic acid mononucleotide, quinolinic acid, 3-hydroxyanthranilate, 3-hydroxykynurenine, kynurenine, N-formylkynurenine, or a pharmaceutically acceptable salt thereof.

In some embodiments, where the NAD precursor includes an intermediate of a nicotinamide riboside kinase pathway, such intermediates may include, without limitation, nicotinamide, nicotinamide mononucleotide, or a pharmaceutically acceptable salt thereof.

In some embodiments, where the NAD precursor includes an intermediate of a nicotinamide riboside kinase pathway, the intermediate may include, without limitation, nicotinamide riboside, nicotinic acid riboside, or a pharmaceutically acceptable salt thereof.

In some embodiments, the NAD precursor may be selected from the group consisting of tryptophan, nicotinic acid, nicotinic acid riboside, nicotinamide riboside (NR), nicotinamide, NADP, and NAD itself, and a pharmaceutically acceptable salt thereof.

In some embodiments, the methods may include administering an inhibitor of NAD consumption. The inhibitor of NAD consumption may include one or more of a poly adp-ribose polymerase (PARP) inhibitor, a CD38 inhibitor, and a pharmaceutically acceptable salt thereof. In some embodiments, a PARP inhibitor may include, but is not limited to, one or more of iodonitrocoumarin, 5-iodo-6-nitrocoumarin, 3,4-dihydro-5-methyl-isoquinolinone 4-amino-1,8-naphthalimide, 3-methoxybenzamide, 8-hydroxy-2-methyl-3-hydro-quinazolin-4-one, 3-(4-chlorophenyl)-quinoxaline-5-carboxamide, 2-(3'-methoxyphenyl)benzimidazole-4-carboxamide, benzamide, 3-aminobenzamide, 3-aminophtalhydrazide, and 1,5-dihydroxyisoquinoline, and the pharmaceutically acceptable salts thereof.

The term "pharmaceutically acceptable salt" refers to salts derived from a variety of organic and inorganic counter ions known in the art. Pharmaceutically acceptable acid addition salts can be formed with inorganic acids and organic acids. Certain inorganic acids from which salts can be derived include, for example, hydrochloric acid, hydrobromic acid, sulfuric acid, nitric acid and phosphoric acid. Certain organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid and salicylic acid. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese and aluminum. Organic bases from which salts can be derived include, for example, primary, secondary, and tertiary amines, substituted amines including naturally occurring substituted amines, cyclic amines and basic ion exchange resins. Specific examples include isopropylamine, trimethylamine, diethylamine, triethylamine, tripropylamine, and ethanolamine. A pharmaceutically acceptable base addition salt is chosen from ammonium, potassium, sodium, calcium, and magnesium salts.

Sirt1 Activation. Liver regeneration may be enhanced by combining an agent that increases NAD activity with an agent that increases Sirt1 activity. In some embodiments, the invention includes methods for enhancing liver regeneration in a mammal in need thereof by administering a therapeutically effective amount of an agent that increases nicotinamide adenine dinucleotide (NAD) activity and a Sirt1 agonist. Accordingly, a therapeutically effective amount of an agent that increases nicotinamide adenine dinucleotide (NAD) activity and a Sirt1 agonist may be co-administered to a patient in need thereof.

As used herein, The terms "co-administration," "co-administering," "administered in combination with," "administering in combination with," "simultaneous," and "concurrent," encompass administration of two or more active pharmaceutical ingredients (in a preferred embodiment of the invention, for example, at least one agent that increases NAD activity and at least one agent that increases Sirt1 activity) to a subject so that both active pharmaceutical ingredients and/or their metabolites are present in the subject at the same time. Co-administration includes simultaneous administration in separate compositions, administration at different times in separate compositions, or administration in a composition in which two or more active pharmaceutical ingredients are present. Simultaneous administration in separate compositions and administration in a composition in which both agents are present are preferred.

As used herein, the term "agonist" refers to a compound or molecule agent that increases the biological activity of a protein or molecule. A "Sirt1" agonist, for example, increases the biological activity of Sirt1. An agonist can stimulate the enzymatic activity of the Sirt1 protein, or it can lead to increased expression of Sirt1 through increased transcription and/or translation. Examples of Sirt1 agonists are known and may include, for example, small molecules, activating antibodies, proteins (e.g., enzymatic co-activators), and upstream effector signals. An agonist can either activate Sirt1 activity directly or indirectly through other effector molecules. Examples of Sirt1 agonists (i.e., agents that increase Sirt1 activity), include, for example, resveratrol, SRT2104 (GSK2245840), SRT1460, butein, fisetin, isonicotinamide (IsoNAM), piceatannol, and quercetin. In some embodiments, the Sirt1 agonist is selected from the group consisting of resveratrol, SRT2104, SRT1460, and a combination thereof. The structures of such compounds are as follows:

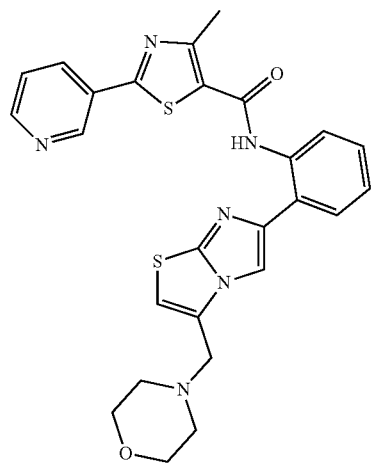

SRT2104

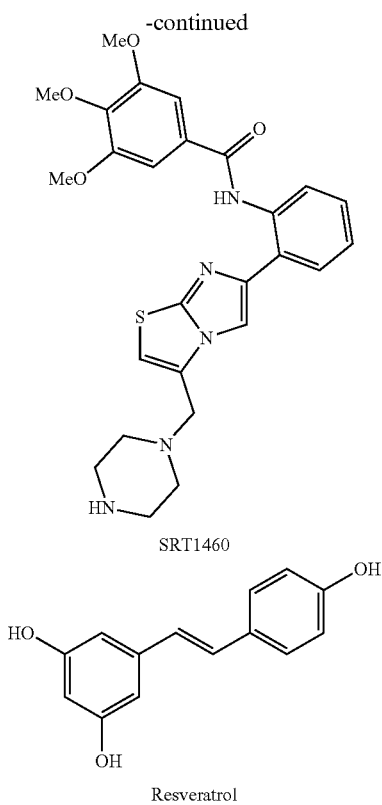

SRT1460

Resveratrol

Examples of Sirt1 agonists are further provided and described in Bonkowski, et al., Nature Reviews (2016) 17: 679-690, U.S. Patent Application Publication Nos. 2011/0015192 and 2013/0338178, and U.S. Pat. Nos. 7,829,556 and 8,247,565, the entirety of which are incorporated herein by reference.

Liver Disease, Disorder, or Injury. The methods of the invention enhance liver regeneration in a mammal in need thereof. The methods of the invention may include the administration of a therapeutically effective amount of an agent or agents (e.g., at least one agent that increases NAD activity and/or at least one agent that increases Sirt1 activity), as described herein. The methods may include the administration of a therapeutically effective amount of an agent when the mammal has liver injury. The methods may also include the administration of a therapeutically effective amount of an agent before liver injury and/or after liver injury.

As used herein, "liver regeneration" refers to replication of existing liver cells or improvement in function of existing liver cells.

As used herein, the term "liver injury" may refer to damage to a liver that may include traumatic liver injury (e.g., liver damage caused by a traumatic event or accident), surgical liver resection (e.g., surgery performed to remove a selected portion of the liver), cirrhosis, liver fibrosis, liver infection, liver transplant, liver damage resulting from bile duct injury, and chemical-induced liver injury. Chemical-induced liver injury may include damage to a liver that is caused by hepatotoxic chemicals or the result of poisoning of the liver by one or more chemicals. For example, chemical-induced liver injury may include liver damage caused by acetaminophen and alcohol or the metabolic by-products thereof.

Administration of an agent in the invention may be accomplished by any means known to a person skilled in the art. The agents used in practicing the methods of the invention may be administered in an amount sufficient to induce the desired therapeutic effect in the recipient thereof. Thus the term "therapeutically effective amount" as used herein refers to an amount of an agent or agents which are sufficient to (1) enhance or otherwise accelerate liver regeneration in a mammal as compared to a similarly situated mammal in the absence of such amount of the agent or agents; and/or (2) bring about a detectable therapeutic, preventative, or ameliorative effect. A therapeutically effective amount may vary depending upon the intended application (in vitro or in vivo), or the patient and disease condition being treated (e.g., the weight, age and gender of the patient), the severity of the disease condition, the manner of administration, etc. which can readily be determined by one of ordinary skill in the art. The term also applies to a dose that will induce a particular response in target cells, tissues, or proteins. The specific dose will vary depending on the particular compounds chosen, the dosing regimen to be followed, whether the compound is administered in combination with other compounds, timing of administration, the tissue to which it is administered, and the physical delivery system in which the compound is carried.

As used herein, the terms "administer," "administration" or "administering" refer to (1) providing, giving, dosing, and/or prescribing by either a health practitioner or his authorized agent or under his or her direction according to the disclosure; and/or (2) putting into, taking or consuming by the mammal, according to the disclosure.

As used herein, the terms "treat," "treatment," and/or "treating" may refer to the management of a disease, disorder, injury, or pathological condition (e.g., liver injury) with the intent to cure, ameliorate, stabilize, prevent, or control the disease, disorder, or pathological condition (e.g., liver injury). Treatment may also include intervention to enhance liver regeneration in a mammal either before or after liver injury, as described herein.

In some embodiments, the methods of the invention may include the administration of a therapeutically effective amount of an agent about 6 months, or about 5 months, or about 4 months, or about 3 months, or about 2 months, or about 1 month, or about 3 weeks, or about 2 weeks, or about 1 week, or about 6 days, or about 5 days, or about 4 days, or about 3 days, or about 2 days, or about 1 day, or about 1 to 23 hours before liver injury.

In some embodiments, the methods of the invention may include the administration of a therapeutically effective amount of an agent about 1 to 23 hours, or about 1 day, or about 2 days, or about 3 days, or about 4 days, or about 5 days, or about 6 days, or about 1 week, or about 2 weeks, or about 3 weeks, or about 1 month, or about 2 months, or about 3 months, or about 4 months, or about 5 months, or about 6 months after liver injury.

In some embodiments, the methods of the invention may include administering a therapeutically effective amount of the agent to a mammal on an hourly basis, or on a daily basis (e.g., once daily, twice daily, thrice daily, etc.), or on a weekly basis (e.g., once weekly, twice weekly, thrice weekly, etc.), or on a monthly basis.

In some embodiments, the methods of the invention may include administering a therapeutically effective amount of the agent to a mammal according to one or more routes of administration. In certain embodiments, the route of administration may be selected from the group consisting of: buccal, dental, endocervical, intramuscular, inhalation, intracranial, intralymphatic, intraocular, intraperitoneal, intrapleural, intrathecal, intratracheal, intrauterine, intravascular, intravenous, intravesical, intranasal, ophthalmic, oral, otic, biliary perfusion, cardiac perfusion, periodontal, rectal, spinal, subcutaneous, sublingual, topical, intravaginal, transdermal, ureteral, urethral, and a combination thereof. In selected embodiments, the route of administration is oral. In some embodiments, for example, administration of a therapeutically effective amount of the agent to a mammal may include inclusion of the agent in diet of the mammal by placing the agent in the mammal's food and/or drinking water.

In some embodiments, the methods of the invention may include administering a therapeutically effective amount of the agent to a mammal in a dosage form selected from the group consisting of a bolus, aerosol, a metered aerosol, a chewable bar, capsule, capsule containing coated pellets, capsule containing delayed release pellets, capsule containing extended release pellets, concentrate, cream, augmented cream, suppository cream, disc, dressing, elixir, emulsion, enema, extended release fiber, extended release film, gas, gel, metered gel, granule, delayed release granule, effervescent granule, chewing gum, implant, inhalant, injectable, injectable lipid complex, injectable liposomes, insert, extended release insert, intrauterine device, jelly, liquid, extended release liquid, lotion, augmented lotion, shampoo lotion, oil, ointment, augmented ointment, paste, pastille, pellet, powder, soap solution, solution for slush, solution/drops, concentrate solution, gel forming solutions/drops, sponge, spray, metered spray, suppository, suspension, suspension/drops, extended release suspension, swab, syrup, tablet, chewable tablet, tablet containing coated particles, delayed release tablet, dispersible tablet, effervescent tablets, extended release tablets, orally disintegrating tablet, tampon, tape, and troche/lozenge.

In some embodiments, the methods of the invention may include administering a therapeutically effective amount of the agent to a mammal at a dosage that is equal to or less than 10 g/kg, 9.5 g/kg, 9.0 g/kg, 8.5 g/kg, 8.0 g/kg, 7.5 g/kg, 7.0 g/kg, 6.5 g/kg, 6.0 g/kg, 5.5 g/kg, 5.0 g/kg, 4.5 g/kg, 4.0 g/kg, 3.5 g/kg, 3.0 g/kg, 2.5 g/kg, 2.0 g/kg, 1.5 g/kg, 1.0 g/kg, 0.95 g/kg, 0.9 g/kg, 0.85 g/kg, 0.8 g/kg, 0.75 g/kg, 0.7 g/kg, 0.65 g/kg, 0.6 g/kg, 0.55 g/kg, 0.5 g/kg, 0.45 g/kg, 0.4 g/kg, 0.35 g/kg, 0.3 g/kg, 0.25 g/kg, 0.2 g/kg, 0.15 g/kg, 0.1 g/kg, 0.09 g/kg, 0.08 g/kg, 0.07 g/kg, 0.06 g/kg, 0.05 g/kg, 0.04 g/kg, 0.03 g/kg, 0.02 g/kg, 0.01 g/kg, 0.009 g/kg, 0.008 g/kg, 0.007 g/kg, 0.006 g/kg, 0.005 g/kg, 0.004 g/kg, 0.003 g/kg, 0.002 g/kg, 0.001 g/kg, 0.0009 g/kg, 0.0008 g/kg, 0.0007 g/kg, 0.0006 g/kg, 0.0005 g/kg, 0.0004 g/kg, 0.0003 g/kg, 0.0002 g/kg, or 0.0001 g/kg, by weight, where "g/kg" is understood to mean weight (g) of agent per weight (kg) of mammal.

In some embodiments, the methods of the invention may include administering a therapeutically effective amount of the agent to a mammal at a dosage that is more than 0.0001 g/kg, 0.0002 g/kg, 0.0003 g/kg, 0.0004 g/kg, 0.0005 g/kg, 0.0006 g/kg, 0.0007 g/kg, 0.0008 g/kg, 0.0009 g/kg, 0.001 g/kg, 0.0015 g/kg, 0.002 g/kg, 0.0025 g/kg, 0.003 g/kg, 0.0035 g/kg, 0.004 g/kg, 0.0045 g/kg, 0.005 g/kg, 0.0055 g/kg, 0.006 g/kg, 0.0065 g/kg, 0.007 g/kg, 0.0075 g/kg, 0.008 g/kg, 0.0085 g/kg, 0.009 g/kg, 0.0095 g/kg, 0.01 g/kg, 0.015 g/kg, 0.02 g/kg, 0.025 g/kg, 0.03 g/kg, 0.035 g/kg, 0.04 g/kg, 0.045 g/kg, 0.05 g/kg, 0.055 g/kg, 0.06 g/kg, 0.065 g/kg, 0.07 g/kg, 0.075 g/kg, 0.08 g/kg, 0.085 g/kg, 0.09 g/kg, 0.095 g/kg, 0.1 g/kg, 0.15 g/kg, 0.2 g/kg, 0.25 g/kg, 0.3 g/kg, 0.35 g/kg, 0.4 g/kg, 0.45 g/kg, 0.5 g/kg, 0.55 g/kg, 0.6 g/kg, 0.65 g/kg, 0.7 g/kg, 0.75 g/kg, 0.8 g/kg, 0.85 g/kg, 0.9 g/kg, 0.95 g/kg, 1 g/kg, 1.5 g/kg, 2 g/kg, 2.5 g/kg, 3 g/kg, 3.5 g/kg, 4 g/kg, 4.5 g/kg, 5 g/kg, 5.5 g/kg, 6 g/kg, 6.5 g/kg, 7 g/kg, 7.5 g/kg, 8 g/kg, 8.5 g/kg, 9 g/kg, 9.5 g/kg, or 10 g/kg, by weight, where "g/kg" is understood to mean weight (g) of agent per weight (kg) of mammal.

Kits of the Invention

In accordance with the foregoing methods of the invention, a kit may be provided that may include one or more agents (e.g., at least one agent that increases NAD activity and/or at least one agent that increases Sirt1 activity) in unit dosage form. The kit according to the invention may be used in the methods as described herein. In some embodiments, the kit may include instructions for use of the agents according to the methods of the invention.

Pharmaceutical Compositions of the Invention

In some embodiments, the invention includes a pharmaceutical composition for enhancing liver regeneration in a mammal in need thereof. In certain embodiments, the pharmaceutical composition may include one or more agents (e.g., at least one agent that increases NAD activity and/or at least one agent that increases Sirt1 activity) and a physiologically compatible carrier medium.

In some embodiments, the concentration of any agent provided in the pharmaceutical compositions of the invention is less than, for example, 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v or v/v of the pharmaceutical composition.

In some embodiments, the concentration of any agent provided in the pharmaceutical compositions of the invention is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v, or v/v of the pharmaceutical composition.

In some embodiments, the concentration of any agent in the pharmaceutical compositions is in the range from about 0.0001% to about 50%, about 0.001% to about 40%, about 0.01% to about 30%, about 0.02% to about 29%, about 0.03% to about 28%, about 0.04% to about 27%, about 0.05% to about 26%, about 0.06% to about 25%, about 0.07% to about 24%, about 0.08% to about 23%, about 0.09% to about 22%, about 0.1% to about 21%, about 0.2% to about 20%, about 0.3% to about 19%, about 0.4% to about 18%, about 0.5% to about 17%, about 0.6% to about 16%, about 0.7% to about 15%, about 0.8% to about 14%, about 0.9% to about 12% or about 1% to about 10% w/w, w/v or v/v of the pharmaceutical composition.

In some embodiments, the concentration of any agent provided in the pharmaceutical compositions is in the range from about 0.001% to about 10%, about 0.01% to about 5%, about 0.02% to about 4.5%, about 0.03% to about 4%, about 0.04% to about 3.5%, about 0.05% to about 3%, about 0.06% to about 2.5%, about 0.07% to about 2%, about 0.08% to about 1.5%, about 0.09% to about 1%, about 0.1% to about 0.9% w/w, w/v or v/v of the pharmaceutical composition.

In some embodiments, the amount of any agent provided in the pharmaceutical compositions is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of agent provided in the pharmaceutical compositions is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

The agents according to the invention are effective over a wide dosage range. For example, in the treatment of certain mammals, dosages independently ranging from 0.001 to 100 g, from 0.01 to 75 g, from 0.1 to 50 g, and 1 to 50 g per day are examples of dosages that may be used. Alternatively, in the treatment of certain mammals, dosages independently ranging from 0.01 to 1000 mg, from 0.5 to 500 mg, and from 1 to 50 mg per day are examples of dosages that may be used. The exact dosage will depend upon the route of administration, the form in which the agent is administered, the gender and age of the mammal to be treated, the body weight of the subject to be treated, and the preference and experience of the attending physician.

As used herein, the term "physiologically compatible carrier medium" includes any and all solvents, diluents, or other liquid vehicle, dispersion or suspension aids, surface agent agents, isotonic agents, thickening or emulsifying agents, preservatives, solid binders, lubricants, fillers and the like as suited for the particular dosage form desired. Remington: The Science and Practice of Pharmacy, 20th edition, A. R. Genaro et al., Part 5, Pharmaceutical Manufacturing, pp. 669-1015 (Lippincott Williams & Wilkins, Baltimore, Md./Philadelphia, Pa.) (2000) discloses various carriers used in formulating pharmaceutical compositions and known techniques for the preparation thereof. Except insofar as any conventional pharmaceutical carrier medium is incompatible with either the agents used in the invention, such as by producing an undesirable biological effect or otherwise interacting in a deleterious manner with any other component(s) of a formulation comprising such compounds or agents, its use is contemplated to be within the scope of this invention. In certain embodiments, the physiologically compatible carrier medium may be water.

In some embodiments, the pharmaceutical composition may be prepared in unit dosage form. In certain embodiments, the unit dosage form may include the physiologically compatible carrier medium and may be selected from the group consisting of a bolus, aerosol, a metered aerosol, a chewable bar, capsule, capsule containing coated pellets, capsule containing delayed release pellets, capsule containing extended release pellets, concentrate, cream, augmented cream, suppository cream, disc, dressing, elixir, emulsion, enema, extended release fiber, extended release film, gas, gel, metered gel, granule, delayed release granule, effervescent granule, chewing gum, implant, inhalant, injectable, injectable lipid complex, injectable liposomes, insert, extended release insert, intrauterine device, jelly, liquid, extended release liquid, lotion, augmented lotion, shampoo lotion, oil, ointment, augmented ointment, paste, pastille, pellet, powder, soap solution, solution for slush, solution/drops, concentrate solution, gel forming solutions/drops, sponge, spray, metered spray, suppository, suspension, suspension/drops, extended release suspension, swab, syrup, tablet, chewable tablet, tablet containing coated particles, delayed release tablet, dispersible tablet, effervescent tablets, extended release tablets, orally disintegrating tablet, tampon, tape, and troche/lozenge The methods, kits, and pharmaceutical compositions of the invention are useful in treating mammals. Such mammals include humans as well as non-human mammals. Non-human mammals include, for example, companion animals such as dogs and cats, agricultural animals such as livestock including cows, horses and the like, and exotic animals, such as zoo animals. However, in certain embodiments, the mammals are humans.

The invention demonstrates that a supplemental NAD precursor can improve the outcome in an experimental model of liver injury. However, recovery from partial hepatectomy may also be influenced by the expression level of Nampt in hepatocytes, and poor regeneration in some mammals lacking Nampt is completely rescued by nicotinamide riboside.

Transient hepatic steatosis is a characteristic feature of liver regeneration. In other experimental settings, Nampt has been suggested to confer resistance to hepatic steatosis via NAD synthesis. These findings are in good agreement with the present observation that steatosis is almost completely absent at 48 hours after PHx in mice given NR or overexpressing Nampt in hepatocytes. Some steatosis was visible in NR-treated mice at 36 hours post-PHx, which suggest the possibility that lipids still accumulate during regeneration in the presence of enhanced NAD synthesis, but are cleared more quickly. This would be consistent with a model where lipids are processed by the regenerating liver in an NAD-sensitive manner to provide a source of energy while sparing glucose for output into the blood stream or use as a metabolic precursor. In the absence of sufficient NAD concentration, lipid oxidation and consequently ATP levels would fall, halting cell proliferation.

Without being limited to any one theory of the invention, while increasing NAD availability might improve regeneration solely through its role as a cofactor for enzymes directly involved in ATP production and/or by sparing precursors for nucleic acid synthesis, it could also act via its role as a cosubstrate for signaling enzymes, including the sirtuins. In this regard, Nampt is known to influence the deacetylase activity of the sirtuin 1 (Sirt1). Recent studies have suggested roles for Sirt1 in both hepatic lipid metabolism and liver regeneration. Old mice with impaired liver regeneration express low hepatic Sirt1, and that ectopically expressing Sirt1 restores hepatocyte proliferation in response to partial hepatectomy in old mice whereas knockdown of Sirt1 impairs regeneration in young mice. In contrast, young mice overexpressing Sirt1 have increased mortality following partial hepatectomy due to defects in bile acid regulation. Nampt expression reduces hepatocyte triglyceride levels in uninjured livers, and that the effect is correlated with increased Sirt1 activity as well as phenocopied by overexpressing Sirt1. Accordingly, and without limited to any one theory of the invention, the reduction in steatosis that we observe with enhanced NAD regeneration may reflect a Sirt1-dependent effect on lipid metabolism. In addition, resveratrol, a small polyphenol that activates Sirt1, has been shown to improve hepatocyte survival in injury models, but also to slow replication.

Overall, the invention demonstrates that NAD metabolism can be modulated to promote recovery from liver injury.

The following examples describe the invention in further detail. These examples are provided for illustrative purposes only, and should in no way be considered as limiting the invention.

EXAMPLES

To directly test whether NAD availability is limiting for liver regeneration, partial hepatectomy, a well-established model for liver injury, was performed in mice given the NAD precursor nicotinamide riboside (NR) in the drinking water. To probe the role of NAD metabolism more specifically in hepatocytes, genetic strategies were employed to overexpress or delete Nicotinamide phosphoribosyltransferase (Nampt), a rate-limiting enzyme for NAD biosynthesis. The results demonstrate that NAD availability is indeed limiting for liver regeneration and suggest that strategies to increase hepatic NAD content may be protective against liver injuries or toxic insults.

Animals, housing and drug treatment: Mice overexpressing Nampt in hepatocytes were obtained by crossing animals carrying an exogenous copy of the Nampt cDNA separated from the CAGGS promoter by a floxed stop cassette that were backcrossed to the C57BL/6J background (as described previously), with mice carrying Albumin-Cre (JAX strain B6.Cg-Tg(Alb-cre)21Mgn/J, stock number 003574). Littermates lacking Albumin Cre were used as controls. For studies on the adult onset of Nampt overexpression, 8-9 week old male Nampt$^{fl/fl}$ and Nampt$^{wt/wt}$ mice were injected with adeno-associated virus in the retroorbital plexus expressing either Cre recombinase (AAV-Cre) or enhanced green fluorescent protein (AAV-Gfp) under the control of thyroxine-binding globulin (Tbg) promoter (AAV-Cre). Nampt$^{fl/fl}$ mice injected with AAV-Gfp and Nampt$^{wt/wt}$ injected with AAV-Cre served as controls. For inducible deletion of Nampt, mice originally created by Oberdan Leo at Université de Liège and backcrossed to the C57/BL6 background were employed and generously provided by Shin-Ichiro Imai at Washington University. As above, 8-9 week old male mice bearing two floxed alleles were injected retroorbitally with adeno-associated virus expressing either Cre recombinase (AAV-Cre) or enhanced green fluorescent protein (AAV-Gfp) under the control of thyroxine-binding globulin (Tbg) promoter. Fasting blood glucose was measured and partial hepatectomies were performed at >14 days after AAV infection in both the adult onset overexpression and liver-specific knock out cohorts. Animals were housed in groups of 4-5 mice/cage in pathogen-free barrier facility in a 12 h light-dark cycle with free access to food and water. For experiments containing only wild type animals, male C57BL/6J mice were ordered directly from Jackson Labs. For nicotinamide riboside (NR) (Chromadex Inc.) supplementation experiments, NR was dissolved in the drinking water at 3.0 mg/ml in light-protected bottles and was changed every 3 days. For fasting and re-feeding experiments, animals were fasted for 16 h with access to water ad libitum in cages containing Alpha-dri bedding. All animal work was performed in accordance with the U.S. Department of Health and Human Services Guide for the Care and Use of Laboratory Animals and with the approval of the University of Pennsylvania Institutional Animal Care and Use Committee.

Partial hepatectomy: 10-14 week old male transgenic mice underwent partial hepatectomy (PHx) according to the protocol of Mitchell and Willenbring between 8 AM and noon. Briefly, after isofluorane anesthesia, a ventral midline incision was made. Then the median and left lateral lobes, comprising 70% of the liver, were resected by pedicle ligation. For EdU (5-ethynyl-2'-deoxyuridine) labeling (Molecular probes), mice were injected intraperitoneally with the labeling reagent at a dose of 16 mg/kg, 5 h before sacrifice. Animals were sacrificed at 36 h or 48 h after PHx, as indicated. The resected and regenerating livers were snap frozen in liquid nitrogen, fixed in 4% paraformaldehyde, embedded in OCT medium (Tissue-TEK O.C.T compound, Sakura), or rapidly frozen in pre-chilled metal clamps in liquid nitrogen for NAD and ATP assays. All surgical procedures involving mice were approved by the Institutional Animal Care and Use Committee protocols of the University of Pennsylvania.

Histology, Immunohistochemistry, and Immunofluorescence: Mitotic figures were counted in Hematoxylin and eosin stained slides. Paraffin embedded liver sections of 5 µm thickness were deparaffinized in Xylene followed by rehydration through a graded ethanol series were stained with Gill 3 hematoxylin (Thermo Scientific) and eosin (Sigma). Mitotically active areas were first screened under lower magnification. For quantification, total mitotic counts in 10 high power fields (40×) in the most mitotically active areas were considered. Representative photomicrographs were taken at 400× magnification using a light microscope coupled with a digital image acquisition system. For immunofluorescent detection of Nampt expression in paraffin sections, antigens were retrieved in R-buffer (Electron Microscopy Sciences Ct #62706-10) followed by quenching and blocking in Cas-Block (Invitrogen 00-8120) for 20 min. Slides were then incubated overnight at 4° C. in humidified chamber with primary rabbit polyclonal anti- NAMPT antibody (Bethyl Laboratories, dilution 1:1000). Goat anti-rabbit IgG (Alexa Fluor 488) was used as secondary antibody at dilution of 1:600 and slides were counter-stained with DAPI (Vector laboratories). For quantification, cells were examined and imaged using a Zeiss Axioplan 2 imaging system under a 20× objective taking both the central and portal venous areas.

EdU staining: Paraffin-embedded liver sections were stained for EdU using either Click-iT EdU Alexa Fluor 488 or Alexa Fluor 594 Imaging Kit (Molecular Probes) according to manufacturer's protocol and 5-6 random areas of each liver were imaged. The fraction of EdU positive hepatocytes was determined by counting manually at 200× in both central vein and portal triad regions and normalizing the DAPI counterstain.

Oil Red O staining: Liver samples frozen in OCT were sectioned at 5 µm thickness and fixed in 10% Neutral Buffered Formalin. Slides were placed in propylene glycol (Sigma) for 2 min and then incubated in Oil Red O (Sigma) for 10 min at 60° C. The slides were then transferred to 85% propylene glycol solution for 1 min and counterstained with hematoxylin (Fisher Scientific). Representative images were captured at 200× magnification using a Nikon E600 bright field microscope coupled with a digital image acquisition system.

Immunoblotting: For Western blot analysis, snap frozen liver pieces were lysed in RIPA buffer supplemented with Halt phosphatase inhibitors (Thermo Scientific) and complete protease inhibitors (Roche) in a tissue lyzer (Qiagen). Tissue lysates were pre-clarified by centrifugation at 15,000 g for 15 minutes at 4° C. After denaturation, samples were resolved on 4-15% SDS-PAGE gels, transferred to PVDF membranes (Milipore) on a wet transfer apparatus (Bio-Rad), and probed using anti-NAMPT (Bethyl Laboratories, PBEF (A300-372A), dilution 1:5000) and HRP conjugated β-actin (Abcam, ab49900) antibodies. Immunoreactive proteins were detected by chemiluminescence. Images were captured in a Bio-Rad imaging station using Super Signal West Femto substrates (Pierce).

Gene-expression analysis: Total RNA was extracted from frozen liver with Trizol (Sigma-Aldrich). 1 µg of RNA was reverse transcribed with High Capacity cDNA Reverse Transcription Kit (Applied Biosystems) according to the manufacturer's recommendations. Real time PCR was performed on an Applied Biosystems 7900HT system with SYBR green master mix (Applied Biosystems). Three technical replicates were obtained for each sample and a relative standard curve method was used to quantify the results obtained using gene-specific primers. TATA box binding protein gene (TBP) and B-actin were used as a housekeeping gene.

NAD Metabolite Extraction from Liver: NAD was extracted from 50 mg of pre-cooled clamp frozen liver in 0.6 M perchloric acid at 4° C. using a tissue lyzer (Qiagen) with a metal bead set at 20 Hz for 2 min. The insoluble materials were pelleted by at 15,000 g for 10 min at 4° C. and the clear supernatant was diluted to 1:100 in ice-cold 100 mM phosphate buffer, pH 8. NAD was measured by an enzymatic cycling assay in a 96-well format modified from the procedure of Graeff and Lee 11 as described previously 7. Briefly, the cycling mix was prepared freshly before use, 5 ul of NAD standards or diluted tissue extracts were mixed with 95 µl of cycling mixture comprising of (2% ethanol, 100 g/ml alcohol dehydrogenase, 10 g/ml diaphorase, 20M resazurin, 10 M flavin mononucleotide, 10 mM nicotinamide, 0.1% BSA in 100 mM phosphate buffer, pH 8.0). The cycling reaction was allowed to proceed for 30 min at room temperature, and the concentration of NAD was determined based on the rate of resorufin accumulation, measured as fluorescence at excitation at 544 nm and emission at 590 nm.

Hepatic triglyceride assay: 25 mg of snap frozen liver tissue was extracted in a cell lysis buffer (140 mM NaCl, 50 mM Tris, pH 7.4, 0.1% Triton-X) using a tissue lyser. Samples were centrifuged for 15 min at 14,000 rpm and triglycerides were assayed with a Triglyceride Assay Kit (Stanbio) using glycerol as a standard.

ATP determination: ATP was measured in neutralized acid extracts of ~50 mg of snap frozen liver using ATP determination Kit (Life Technologies) according to the manufacturer's protocol.

Glucose measurement: Blood glucose values were measured from the tail vein using a OneTouch Ultra glucose analyzer after an overnight (16 h) fast.

Statistics: All results are expressed as the mean±SEM. Comparisons between two groups were analyzed using unpaired 2-tailed Student's t test. Comparisons between three or more groups were analyzed using one-way ANOVA in Prism 6 (GraphPad), followed by post-hoc analysis with Student's t test. For correlation matrices, data were analyzed using Pearson correlation coefficients. Differences between means were defined as significant at $P<0.05$.

Example 1

Nicotinamide Riboside Promotes Liver Regeneration

To test whether NAD availability limits the rate of liver regeneration, the drinking water of wild-type C57BL/6J mice was supplemented with NR (3 mg/mL, ~500 mg/kg) beginning 14 days prior to two-thirds partial hepatectomy (PHx). While regenerating livers from control mice were pale with a characteristic mottled pattern by 48 hours post PHx, those from NR-treated mice were more uniformly colored (FIG. 1, panel A) and displayed greatly enhanced hepatocyte proliferation, as assessed by incorporation of EdU into DNA (FIG. 1, panels B and C). This was reflected by a significant improvement in liver mass (FIG. 1, panel D). Notably, changes in the size of the liver in control mice given NR were not observed, and there was no difference in the weights of the resected lobes between the two groups (data not shown). As expected, NAD content was increased in the livers of NR treated mice both pre (~35%) and post (~58%) hepatectomy (FIG. 1, panel E). Analysis of H&E stained sections revealed a 48% increase in mitotic activity in the presence of NR (FIG. 1, panels F and G). Moreover, the fatty changes, characteristic of early stages of liver regeneration, while readily apparent in controls, were not evident in NR treated mice. These include hepatic steatosis characterized by the presence of both micro and macro vesicular lipid droplets (FIG. 1, panels F and H) as well as accumulation of hepatic triglycerides (FIG. 1, panel I). Thus, NR treatment is sufficient to increase hepatic NAD content and significantly promotes liver regeneration while ameliorating fatty changes.

Example 2

Figure 2:
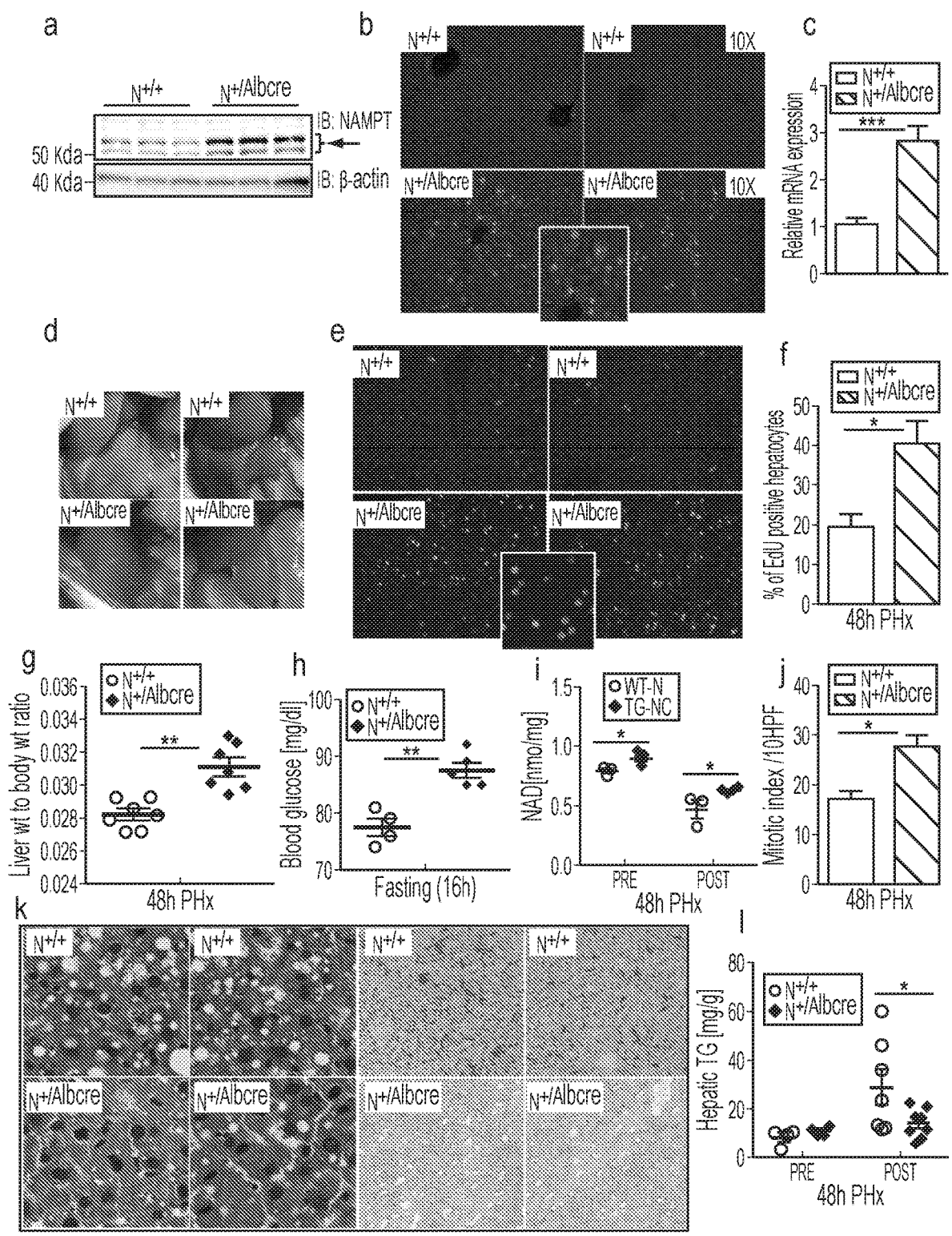
FIG. 2 illustrates that hepatocyte-specific overexpression of Nampt promotes liver regeneration. Mice carrying a Cre-inducible allele of Nampt in addition to Alb-Cre (denoted as $N^{+/Albcre}$) and littermate controls ($N^{+/+}$) were subjected to ⅔ partial hepatectomy and analyzed 48 hours later. (Panel A) Nampt protein and mRNA expression in liver. (panel B) Immunofluorescence showing overexpression of Nampt in peri-portal and peri-central venous areas of $N^{+/Albcre}$ mice. Inset shows an enlarged view of $N^{+/Albcre}$. (panel C) mRNA expression of NAMPT in liver. (panel D) Photo-micrographs of regenerating livers. (panel E) Proliferating hepatocytes identified by EdU detected by immunofluorescence (indicated as green in the assay) and counterstained with DAPI (indicated as blue in the assay). Inset shows an enlarged view of $N^{+/Albcre}$. (panel F) Quantification of EdU positive hepatocytes (n=5/group). (panel G) Liver to body weight ratios. (panel H) Fasting blood glucose. (panel I) Liver NAD content before and after PHx. (panels J and K) Mitotic index as determined by counting mitotic figures in hepatocytes under high power in H&E stained sections. Representative liver sections stained with H&E are shown. (panel L) Hepatic lipid content as determined by Oil Red O and hepatic triglyceride assay. Error bars represent S.E.M. *, p 0.05; , p 0.01; *, p 0.001

Hepatocyte-Specific Nampt Over-Expression Recapitulates the Effects of Systemic NR on Liver Regeneration Because oral NR may have systemic effects that influence the rate of liver regeneration, a test was performed to determine whether NAD synthesis specifically in hepatocytes is sufficient to recapitulate the foregoing observations. A strain of mice that overexpress Nicotinamide phosphoribosyltransferase (Nampt) were employed in a Cre-inducible manner, crossed to mice expressing Cre under the control of the Albumin promoter (FIG. 2, panels A to C). Nampt overexpression was not uniform (FIG. 2, panel B), and was markedly prominent near the pen portal and central venous areas. By 48 hours following PHx, Nampt-overexpressing livers appeared darker and more uniform in color (FIG. 2, panel D) and, as was observed with NR treatment, had dramatically enhanced EdU incorporation (FIG. 2, panels E and F). These changes correlated with an increase in the size of regenerated livers (FIG. 2, panel G). Notably, hepatocyte-specific overexpression of Nampt did not affect body or liver weight prior to surgery, although we noted a mild elevation of fasting glucose levels (FIG. 2, panel H). Liver NAD content was significantly elevated both pre- and post-PHx (FIG. 2, panel I). Mitotic indices were increased, and accumulation of lipid droplets and triglyceride content were dramatically decreased (FIG. 2, panels J to L). Accordingly, liver-specific enhancement of NAD biosynthesis recapitulates the key effects of systemic NR treatment on liver regeneration.

Example 3

Figure 3:
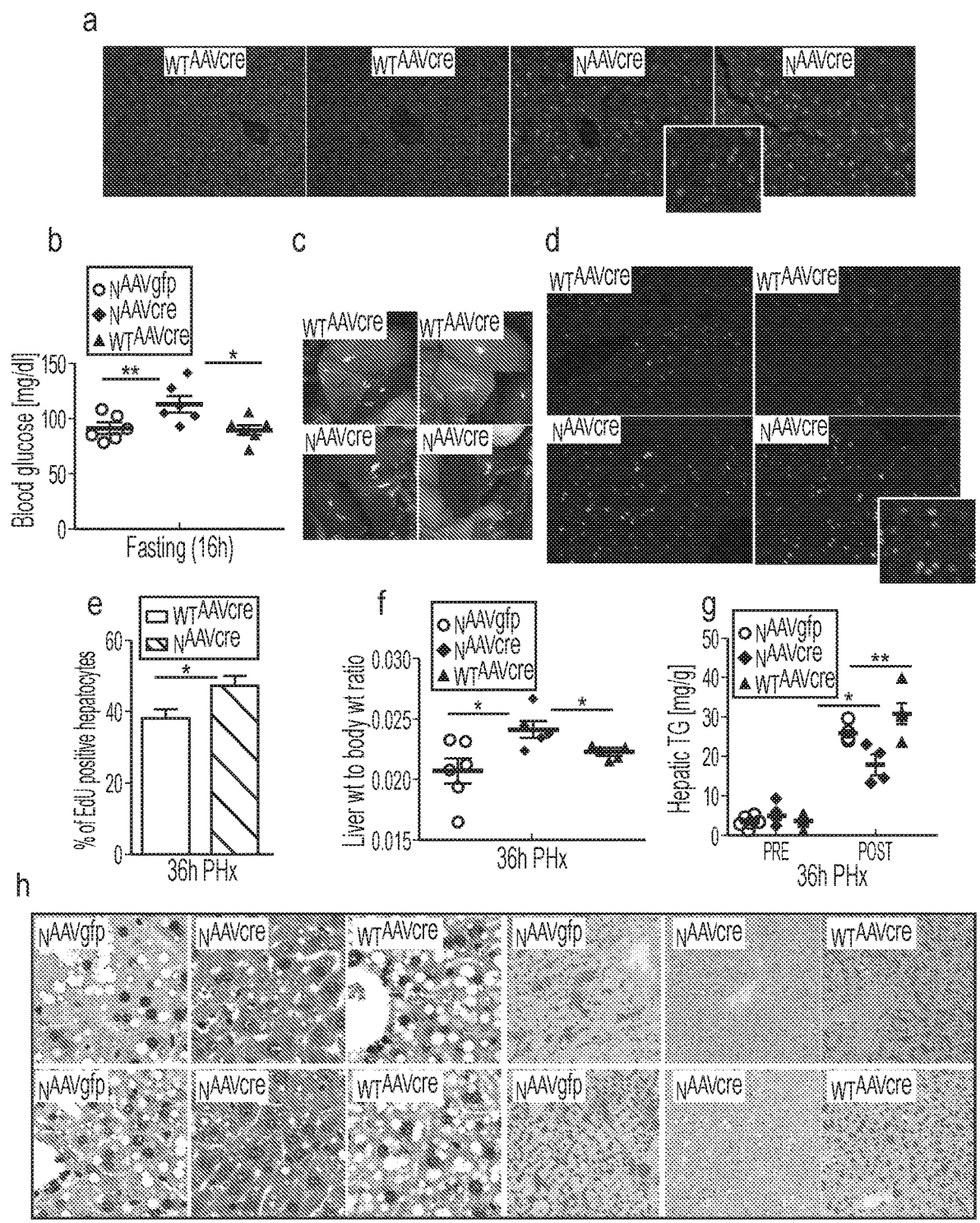
FIG. 3 illustrates that adult onset Nampt over-expression is sufficient for regenerative phenotypes. Mice carrying a Cre-inducible allele of Nampt were infected with AAV-Cre (denoted as $N^{AAVcre}$) and littermate controls ($N^{AAVgfp}$ or $WT^{AAVcre}$) were subjected to ⅔ partial hepatectomy and analyzed 36 hours later. (panel A) Immunofluorescence showing over-expression of Nampt in pen-portal and pen-central venous areas of $N^{AAVcre}$ mice. Inset shows an enlarged view of $N^{AAVcre}$. (panel B) Fasting blood glucose. (panel C) Photo-micrographs of regenerating livers. (panel D) Proliferating hepatocytes identified by EdU detected by immunofluorescence (indicated as green in the assay) and counterstained with DAPI (indicated as blue in the assay). Inset shows an enlarged view of $N^{AAVcre}$. (panel E) Quantification of EdU-positive hepatocytes (n=5/group). (panel F) Liver to body weight ratios. (panel G) Hepatic triglyceride content. (panel H) Right panels: representative liver sections stained with H&E. Left panels: lipid accumulation by Oil Red O. Error bars represent S.E.M. *, p 0.05; , p 0.01; *, p 0.001.

Adult Onset Over-Expression is Sufficient for the Beneficial Effects of Nampt To exclude the possibility that improved regeneration in Nampt-overexpressing mice might be secondary to metabolic adaptations in early life, a second set of experiments were performed in which Cre was delivered via adeno-associated virus (AAV) in adult mice. Nampt overexpressing mice from this experiment were compared to two distinct sets of littermate controls: those carrying the floxed allele and infected with AAV encoding GFP and wild type mice infected with AAV-Cre. Mice that overexpressed Nampt in their livers only during adulthood displayed mildly elevated fasting glucose (FIG. 3, panels A and B) and enhanced hepatocellular proliferation, similar to the results obtained in mice with life-long overexpression (FIG. 3, panels C to F). Whereas the previous group of mice were sacrificed at 48 hours post PHx to allow quantification of mitotic figures, the adult onset group was sacrificed at 36 hours to capture the peak of DNA synthesis. As in the previous experiments, Nampt overexpression attenuated acute hepatic steatosis and accumulation of hepatic triglycerides (FIG. 3, panels G and H).

Example 4

Hepatocyte-Specific Deletion of Nampt Impairs Liver Regeneration and is Completely Rescued by Nicotinamide Riboside (NR)

Figure 4:
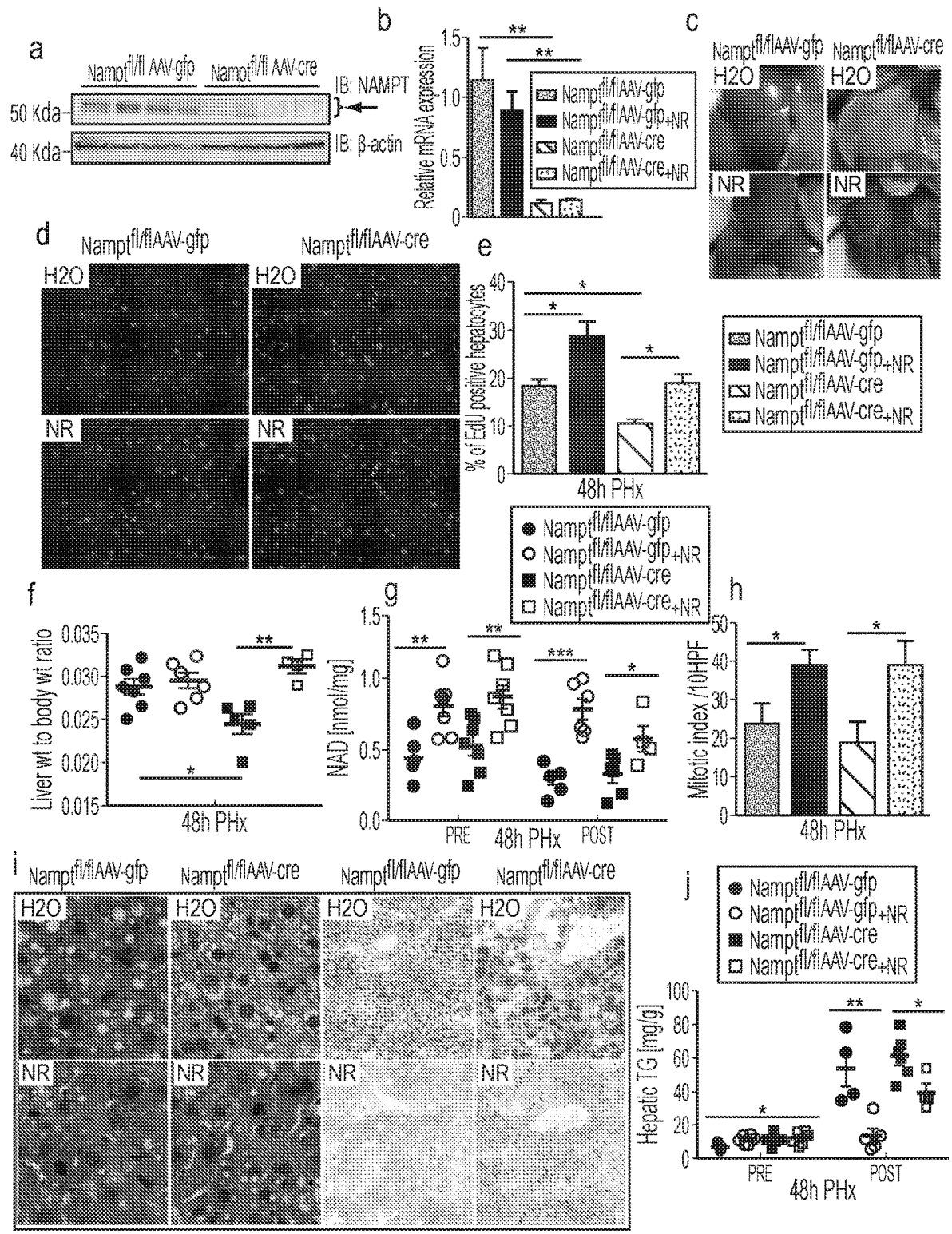
FIG. 4 illustrates that hepatocyte-specific loss of Nampt impairs regeneration, and is rescued by NR. Hepatocyte specific Nampt deficient mice were generated by injecting animals bearing two floxed alleles with an AAV expressing Cre recombinase (AAV-Cre). Littermates infected with AAV-Gfp served as controls. Treatment with NR (~500 mg/kg/day) began 5 days after infection and 2 weeks prior to PHx. Analyses were performed 48 hours after PHx. (panels A and B) Protein and mRNA expression of Nampt in livers. (panel C) Photo-micrographs of regenerating livers. (panel D) Proliferating hepatocytes identified by EdU detected by immunofluorescence (indicated as red in the assay) and counterstained with DAPI (indicated as blue in the assay). (panel E) Quantification of EdU positive hepatocytes (n=5-6/group). (panel F) Liver to body weight ratios. (panel G) NAD content in livers before and after PHx. (panel H) Mitotic index as determined by counting mitotic figures in hepatocytes under high power in H&E stained sections (n=5-6/group). (panel I) Representative liver sections stained with H&E (left panels) and Oil Red O (right panels). (panel J) Hepatic triglyceride content. Error bars represent S.E.M. *, p 0.05; , p 0.01; *, p 0.001.

Nampt is secreted from adipose tissue and immune cells, and the extracellular form (eNampt/PBEF/Visfatin) remains catalytically active. Nampt secretion from primary hepatocytes has also been observed, and therefore, it remains formally possible that overexpression of Nampt in hepatocytes from the transgenic mice leads to spillover into the circulation that could have NAD-dependent effects in other cell types. Moreover, eNampt may have functions that are independent of its catalytic activity, raising the possibility that NR and Nampt overexpression could work through independent pathways to influence liver regeneration. To address these points, hepatocyte-specific Nampt deficient mice were generated by injecting AAV-Cre into adult animals bearing two floxed alleles for Nampt (FIG. 4, panels A and B). Littermates carrying the floxed allele that were infected with AAV-GFP served as controls. Five days after infection, half of the mice in each group were placed on drinking water containing NR and treated for an additional 2 weeks prior to PHx. Macroscopically, regenerated livers of Namptfl/flAAV-Cre mice were pale with petechial hemorrhage, which was prevented by NR treatment (FIG. 4, panel C). Liver regeneration during the first 48 hours after PHx was markedly compromised in the Nampt KO mice, and restored by NR treatment (FIG. 4, panels D to F), which effectively increased NAD content in both genotypes (FIG. 4, panel G). Consistently NR treatment largely restored mitotic index in the Nampt KO mice (FIG. 4, panels H and I), and again there was no change in the weight of the resected lobes, indicating that all livers were normal size prior to injury.

Histological examination revealed dramatic hepatic steatosis in Nampt$^{fl/flAAV-Cre}$ mice, comprising both micro and macro-vesicular lipid droplets (FIG. 4, panel I, upper images). In contrast, NR abolished hepatic lipid accumulation in regenerating wild type livers and nearly normalized hepatic fatty changes in the NAMPT deficient regenerating livers (FIG. 4, panel I, lower images). Hepatic triglycerides were also reduced by ~75% in Nampt$^{fl/flAAV-Gfp}$ and ~35% in Nampt$^{fl/flAAv-Cre}$ mice with NR treatment (FIG. 4, panel J). The results demonstrate that loss of endogenous Nampt expression in hepatocytes impairs liver regeneration and deteriorates lipid metabolism, and that supplementation with an NAD precursor is sufficient to ameliorate these changes.

Example 5

Figure 5:
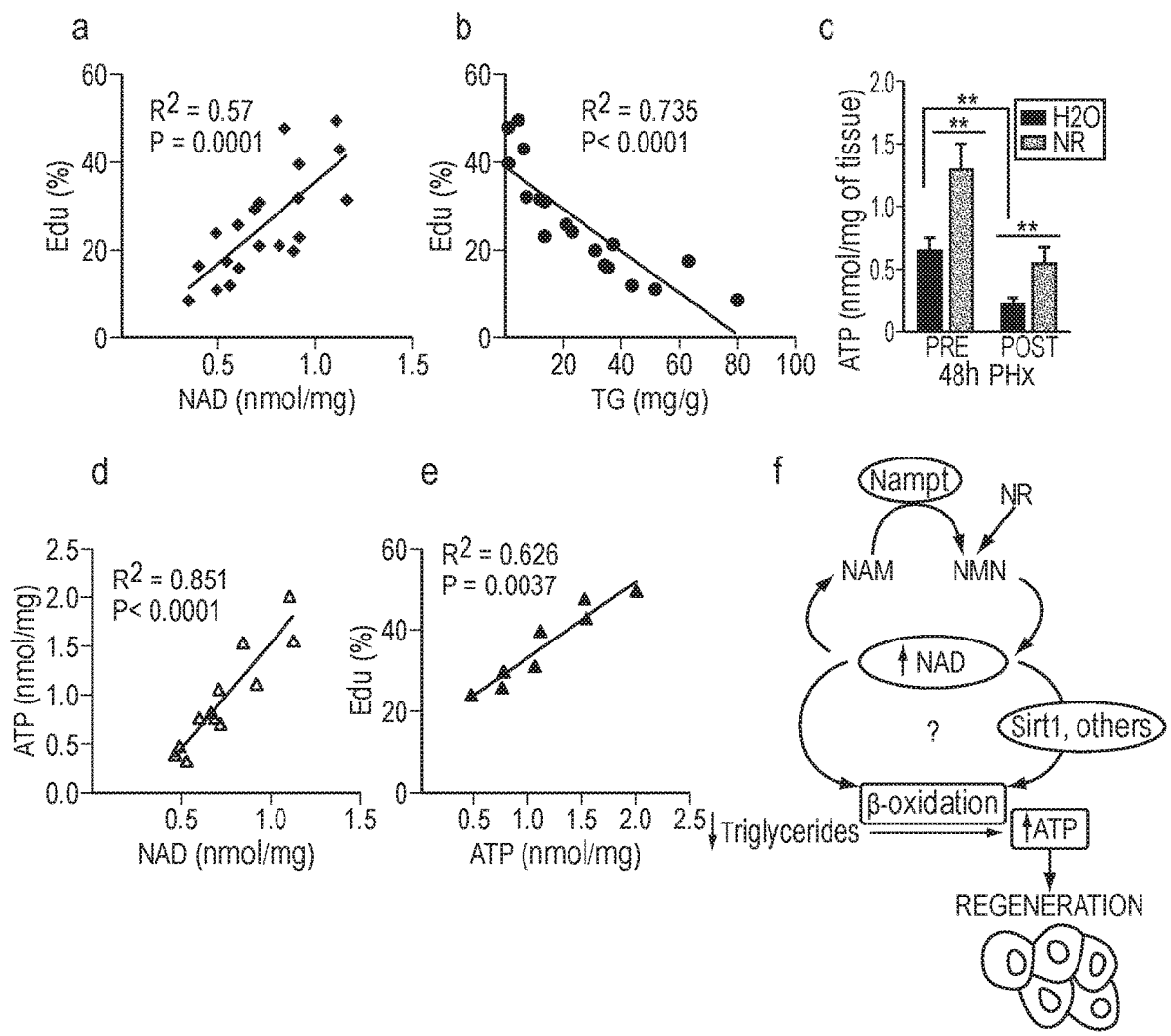
FIG. 5 illustrates that hepatocyte proliferation exhibits a strong correlation with liver NAD concentration and an inverse relationship with hepatic lipid content. Data from individual animals were plotted to study the correlations between NAD, lipid metabolism and hepatocyte proliferation. (panel A) Positive correlation between NAD concentration and hepatocyte proliferation. (panel B) Inverse correlation between hepatocyte proliferation and triglyceride content. (panel C) Liver ATP content assessed in both pre or post hepatectomy in NR treated mice (n=6/group). (panels D and E) Positive correlation between liver ATP content and NAD and hepatocyte proliferation. (panel F) Proposed model of NAD mediated regeneration.

Liver NAD Content Strongly Correlates with Energy Status, Triglyceride Accumulation, and Hepatocyte Proliferation To gain further insight into the relationships between NAD, lipid metabolism and hepatocyte proliferation, a test was provided to determine whether these correlations hold true at the level of individual animals. Hepatocyte proliferation displays a striking positive correlation with liver NAD content and an inverse correlation with hepatic triglycerides (FIG. 5, panels A and B). Without being limited to any one theory, this could reflect the need for optimal NAD levels to allow oxidation of lipids to provide energy for cell growth and division, either due to the direct requirement for NAD in the 3-hydroxyacyl-CoA dehydrogenase (HADH)-catalyzed step of fatty acid oxidation and the tricarboxylic acid cycle (TCA), or due to its role as a cosubstrate for signaling enzymes such as sirtuins. Consistent with this hypothesis, ATP levels were significantly reduced in regenerating livers and enhanced by NR treatment (FIG. 5, panel C). Moreover, ATP content correlated positively with both NAD and hepatocyte proliferation (FIG. 5, panels D and E), suggesting that NR can alleviate the energetic stress imposed by regeneration in the liver.

A proposed model of liver regeneration is depicted in FIG. 5 (panel F). Without being bound to any one theory of the invention, hepatic NAD promotes fatty acid oxidation, thereby generating ATP necessary for hepatocellular growth and regeneration. NAD is directly required in the 3-hydroxyacyl-CoA dehydrogenase (HADH)-catalyzed step of fatty acid oxidation as well as the tricarboxylic acid cycle (TCA), but may also act indirectly via signaling enzymes such as SIRT1, which use NAD as a cosubstrate. NAD concentration can be modulated based on the expression of Nampt, which catalyzes the formation of nicotinamide mononucleotide (NMN) from nicotinamide and phosphoribosylpyrophosphate. Alternatively, NMN can be generated from NR by the action of NR kinase.

Example 6

Hepatocyte Specific Deletion of Sirtuin1 Impairs Regeneration and is Partially Rescued by NR Studies were performed to determine the ability of NR to improve liver regeneration in the context of Sirt1 deletion, which impairs this process.

Figure 6:
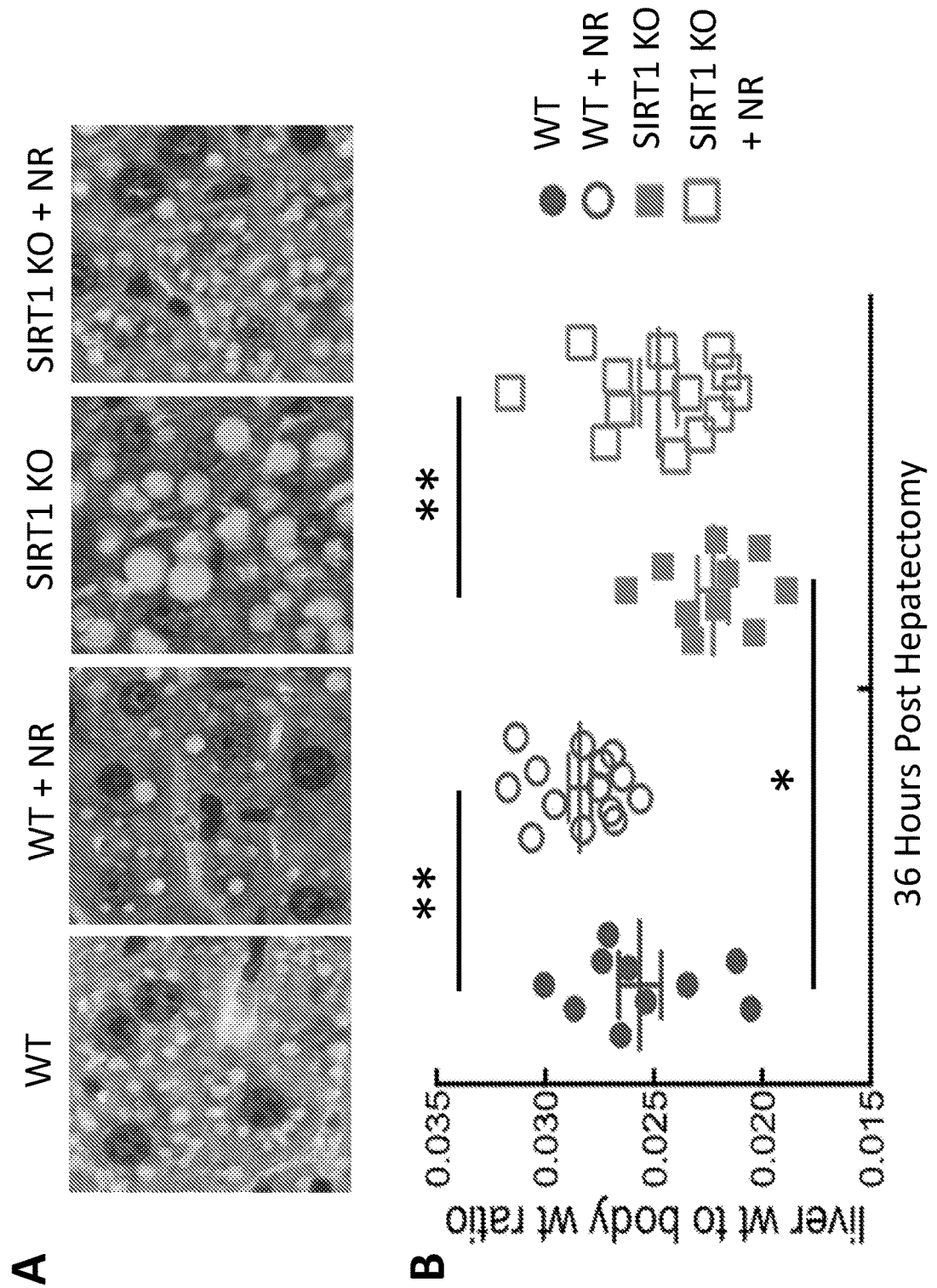
FIG. 6 illustrates that hepatocyte specific deletion of Sirt1 impairs regeneration and is partially rescued by NR as shown in (panel A) a Sirt1 knockout study with NR treated liver sections and (panel B) a liver regeneration study with NR in compromised livers from Sirt1 knockout mice.

Sirt1 knockouts and littermate controls were treated with NR (500 mgs/Kg/day) for 2 weeks prior to partial hepatectomy (PHx). Representative liver sections stained with hematoxylin and eosin revealed acute hepatic steatosis in Sirt1 deficient mice, having both micro and macrovesicular fat droplets (FIG. 6, panel A). NR treatment partially rescued the phenotype and attenuated the hepatic fatty changes.

In another assay, liver regeneration during the first 36 hour post PHx was compromised in Sirt1 knockout mice and restored by NR treatment. NR mediated restoration of liver tissue is depicted as an increase in the size of the regenerated livers as compared to the untreated livers of both wild type and Sirt1 knockout mice (FIG. 6, panel B).

A number of patent and non-patent publications may be cited herein in order to describe the state of the art to which this invention pertains. The entire disclosure of each of these publications is incorporated by reference herein.

While certain embodiments of the invention have been described and/or exemplified above, various other embodiments will be apparent to those skilled in the art from the foregoing disclosure. The invention is, therefore, not limited to the particular embodiments described and/or exemplified, but is capable of considerable variation and modification without departure from the scope and spirit of the appended claims.

Moreover, as used herein, the term "about" means that dimensions, sizes, formulations, parameters, shapes and other quantities and characteristics are not and need not be exact, but may be approximate and/or larger or smaller, as desired, reflecting tolerances, conversion factors, rounding off, measurement error and the like, and other factors known to those of skill in the art. In general, a dimension, size, formulation, parameter, shape or other quantity or characteristic is "about" or "approximate" whether or not expressly stated to be such. It is noted that embodiments of very different sizes, shapes and dimensions may employ the described arrangements.

Furthermore, the transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. All compositions, formulations, kits, and methods described herein that embody the invention can, in alternate embodiments, be more specifically defined by any of the transitional terms "comprising," "consisting essentially of," and "consisting of."

REFERENCES

1. Fan S T, Lo C M, Liu C L, et al. Safety of donors in live donor liver transplantation using right lobe grafts. Arch Surg 2000;135:336-40.
2. Kubota K, Makuuchi M, Kusaka K, et al. Measurement of liver volume and hepatic functional reserve as a guide to decision-making in resectional surgery for hepatic tumors. Hepatology 1997;26:1176-81.
3. Michalopoulos G K. Liver regeneration. J Cell Physiol 2007;213:286-300.
4. Ferris G M, Clark J B. Nicotinamide nucleotide synthesis in regenerating rat liver. Biochem J 1971;121:655-62.
5. Clark J B, Greenbaum A L, McLean P. The concentration and biosynthesis of nicotinamide nucleotides in the livers of rats treated with carcinogens. Biochem J 1966;98: 546-56.
6. Clark J B, Pinder S. Control of the steady-state concentrations of the nicotinamide nucleotides in rat liver. Biochem J 1969;114:321-30.
7. Frederick D W, Davis J G, Davila A, Jr., et al. Increasing NAD synthesis in muscle via nicotinamide phosphoribosyltransferase is not sufficient to promote oxidative metabolism. J Biol Chem 2015;290:1546-58.
8. Yoon M J, Yoshida M, Johnson S, et al. SIRT1-Mediated eNAMPT Secretion from Adipose Tissue Regulates Hypothalamic NAD+ and Function in Mice. Cell Metab 2015;21:706-17.
9. Mitchell C, Willenbring H. A reproducible and well-tolerated method for 2/3 partial hepatectomy in mice. Nat Protoc 2008;3:1167-70.
10. Mitchell C, Willenbring H. Addendum: A reproducible and well-tolerated method for 2/3 partial hepatectomy in mice. Nat Protoc 2014;9.
11. Graeff R, Lee H C. A novel cycling assay for cellular cADP-ribose with nanomolar sensitivity. Biochem J 2002; 361:379-84.
12. Imai S, Kiess W. Therapeutic potential of SIRT1 and NAMPT-mediated NAD biosynthesis in type 2 diabetes. Front Biosci (Landmark Ed) 2009;14:2983-95.
13. Garten A, Petzold S, Korner A, et al. Nampt: linking NAD biology, metabolism and cancer. Trends Endocrinol Metab 2009;20:130-8.
14. Garten A, Petzold S, Barnikol-Oettler A, et al. Nicotinamide phosphoribosyltransferase (NAMPT/PBEF/visfatin) is constitutively released from human hepatocytes. Biochem Biophys Res Commun 2010;391:376-81.
15. Soncini D, Caffa I, Zoppoli G, et al. Nicotinamide phosphoribosyltransferase promotes epithelial-to-mesenchymal transition as a soluble factor independent of its enzymatic activity. J Biol Chem 2014;289:34189-204.
16. Hasmann M, Schemainda I. FK866, a highly specific noncompetitive inhibitor of nicotinamide phosphoribosyltransferase, represents a novel mechanism for induction of tumor cell apoptosis. Cancer Res 2003;63:7436-42.
17. Pauta M, Rotllan N, Fernandez-Hernando A, et al. Akt-mediated FoxO1 inhibition is required for liver regeneration. Hepatology 2015.
18. Rudnick D A. Trimming the fat from liver regeneration. Hepatology 2005;42:1001-3.
19. Rudnick D A, Davidson N O. Functional Relationships between Lipid Metabolism and Liver Regeneration. Int J Hepatol 2012;2012:549241.
20. Tao R, Wei D, Gao H, et al. Hepatic FoxOs regulate lipid metabolism via modulation of expression of the nicotinamide phosphoribosyltransferase gene. J Biol Chem 2011;286:14681-90.
21. Garten A, Schuster S, Penke M, et al. Physiological and pathophysiological roles of NAMPT and NAD metabolism. Nat Rev Endocrinol 2015;11:535-46.
22. Dahl T B, Holm S, Aukrust P, et al. Visfatin/NAMPT: a multifaceted molecule with diverse roles in physiology and pathophysiology. Annu Rev Nutr 2012;32:229-43.
23. Purushotham A, Schug T T, Xu Q, et al. Hepatocyte-specific deletion of SIRT1 alters fatty acid metabolism and results in hepatic steatosis and inflammation. Cell Metab 2009;9:327-38.
24. Garcia-Rodriguez J L, Barbier-Torres L, Fernandez-Alvarez S, et al. SIRT1 controls liver regeneration by 25. Jin J, Iakova P, Jiang Y, et al. The reduction of SIRT1 in livers of old mice leads to impaired body homeostasis and to inhibition of liver proliferation. Hepatology 2011;54:989-98.

26. Wang Y, Jiang Y, Fan X, et al. Hepato-protective effect of resveratrol against acetaminophen-induced liver injury is associated with inhibition of CYP-mediated bioactivation and regulation of SIRT1-p53 signaling pathways. Toxicol Lett 2015;236:82-9.

What is claimed is:

1. A method for enhancing liver regeneration by replication of existing liver cells in a mammal in need thereof, the method comprising administering a therapeutically effective amount of at least one agent selected from the group consisting of nicotinamide riboside (NR) and nicotinamide mononucleotide (NMN).

2. The method according to claim 1, wherein the mammal is about to undergo liver surgery, is at risk for liver injury, or has liver injury.

3. The method according to claim 1, wherein the therapeutically effective amount of the at least one agent is administered before liver injury.

4. The method according to claim 1, wherein the therapeutically effective amount of the at least one agent is administered about 6 months, or about 5 months, or about 4 months, or about 3 months, or about 2 months, or about 1 month, or about 3 weeks, or about 2 weeks, or about 1 week, or about 6 days, or about 5 days, or about 4 days, or about 3 days, or about 2 days, or about 1 day, or about 1 to 23 hours before liver injury.

5. The method according to claim 1, wherein the therapeutically effective amount of the at least one agent is administered after liver injury.

6. The method according to claim 2, wherein the liver injury comprises one or more of traumatic liver injury, cirrhosis, liver fibrosis, liver infection, liver transplant, liver damage resulting from bile duct injury, surgical liver resection, and chemical-induced liver injury.

7. The method according to claim 6, wherein the chemical-induced liver injury comprises one or more of acetaminophen-induced liver injury and alcohol-induced liver injury.

8. The method according to claim 1, wherein administering the therapeutically effective amount of the at least one agent comprises a route of administration selected from the group consisting of buccal, dental, endocervical, intramuscular, inhalation, intracranial, intralymphatic, intraocular, intraperitoneal, intrapleural, intrathecal, intratracheal, intrauterine, intravascular, intravenous, intravesical, intranasal, ophthalmic, oral, otic, biliary perfusion, cardiac perfusion, periodontal, rectal, spinal, subcutaneous, sublingual, topical, intravaginal, transdermal, ureteral, urethral, and a combination thereof.

9. The method according to claim 1, wherein administering the therapeutically effective amount of the at least one agent comprises oral administration.

10. The method according to claim 1, wherein administering the therapeutically effective amount of the at least one agent comprises administering the agent in a dosage form selected from the group consisting of a bolus, aerosol, a metered aerosol, a chewable bar, capsule, capsule containing coated pellets, capsule containing delayed release pellets, capsule containing extended release pellets, concentrate, cream, augmented cream, suppository cream, disc, dressing, elixir, emulsion, enema, extended release fiber, extended release film, gas, gel, metered gel, granule, delayed release granule, effervescent granule, chewing gum, implant, inhalant, injectable, injectable lipid complex, injectable liposomes, insert, extended release insert, intrauterine device, jelly, liquid, extended release liquid, lotion, augmented lotion, shampoo lotion, oil, ointment, augmented ointment, paste, pastille, pellet, powder, soap solution, solution for slush, solution/drops, concentrate solution, gel forming solutions/drops, sponge, spray, metered spray, suppository, suspension, suspension/drops, extended release suspension, swab, syrup, tablet, chewable tablet, tablet containing coated particles, delayed release tablet, dispersible tablet, effervescent tablets, extended release tablets, orally disintegrating tablet, tampon, tape, and troche/lozenge.

11. The method according to claim 1, wherein administering the therapeutically effective amount of the at least one agent comprises administering the agent as a bolus.

12. The method according to claim 1, wherein administering the therapeutically effective amount of the at least one agent comprises hourly, once daily, twice daily, thrice daily, once weekly, twice weekly, thrice weekly, or monthly administration.

13. The method according to claim 1, wherein the at least one agent is nicotinamide riboside (NR).

14. The method according to claim 1, where the at least one agent is nicotinamide mononucleotide (NMN).

15. The method according to claim 14, wherein the administered therapeutically effective amount of nicotinamide mononucleotide (NMN) is from 0.01 to 1000 mg per day.

16. The method according to claim 14, wherein the therapeutically effective amount of nicotinamide mononucleotide (NMN) is administered in a pharmaceutical composition in an amount equal to or less than 2.0 g.

17. The method according to claim 1, wherein the mammal is human.

* * * * *